(12) United States Patent
Miyaji et al.

(10) Patent No.: US 8,749,778 B2
(45) Date of Patent: Jun. 10, 2014

(54) METHOD FOR EVALUATION OF OXIDE SEMICONDUCTOR ELECTRODE, APPARATUS FOR EVALUATION OF OXIDE SEMICONDUCTOR ELECTRODE, AND APPARATUS FOR PRODUCTION OF OXIDE SEMICONDUCTOR ELECTRODE

(75) Inventors: Sae Miyaji, Kanagawa (JP); Go Hirano, Tokyo (JP)

(73) Assignee: Sony Corporation, Tokyo (JP)

( * ) Notice: Subject to any disclaimer, the term of this patent is extended or adjusted under 35 U.S.C. 154(b) by 334 days.

(21) Appl. No.: 13/307,843

(22) Filed: Nov. 30, 2011

(65) Prior Publication Data

US 2012/0140216 A1  Jun. 7, 2012

(30) Foreign Application Priority Data

Dec. 7, 2010  (JP) ................. 2010-272496

(51) Int. Cl.
  *G01J 3/44* (2006.01)
  *H01L 31/00* (2006.01)
  *G01N 21/65* (2006.01)
  *H01L 51/00* (2006.01)
  *H01G 9/20* (2006.01)

(52) U.S. Cl.
  CPC ............ *G01N 21/65* (2013.01); *H01L 51/0031* (2013.01); *H01G 9/2027* (2013.01); *Y02E 10/542* (2013.01)
  USPC .......................................... 356/301; 136/263

(58) Field of Classification Search
  CPC . H01G 9/2059; H01G 9/2031; H01G 9/2027; H01G 9/20; G01N 21/65; H01L 51/0031; Y02E 10/542
  USPC .......................................... 356/301; 136/263
  See application file for complete search history.

(56) References Cited

U.S. PATENT DOCUMENTS

| 6,025,202 A * | 2/2000 | Natan ........................... 436/104 |
| 2010/0154871 A1* | 6/2010 | Ma et al. ....................... 136/252 |
| 2011/0033883 A1* | 2/2011 | Cosgrave et al. .............. 435/29 |
| 2011/0245074 A1* | 10/2011 | Smith et al. ................. 502/309 |

FOREIGN PATENT DOCUMENTS

JP  2004-079610 A  3/2004

OTHER PUBLICATIONS

Lei Miaoa, Sakae Tanemura, Shoichi Tohb, Kenji Kanekob, Masaki Tanemura, "Fabrication, characterization and Raman study of anatase-TiO2 nanorods by a heating-sol—gel template process", Journal of Crystal Growth 264 (2004) 246-252.*

(Continued)

*Primary Examiner* — Gregory J Toatley
*Assistant Examiner* — Violeta A Prieto
(74) *Attorney, Agent, or Firm* — Wolf, Greenfield & Sacks, P.C.

(57) ABSTRACT

Disclosed herein is a method for evaluation of an oxide semiconductor electrode, the method comprising: performing Raman spectrometry on a porous oxide semiconductor layer having a dye adsorbed thereto, thereby acquiring a Raman spectrum having a peak attributable to the dye and a peak attributable to the oxide semiconductor; obtaining from the Raman spectrum a parameter for dye adsorption quantity which is defined by the formula:

Parameter for dye adsorption quantity=(Peak intensity attributable to dye)/(Peak intensity attributable to oxide semiconductor);

and estimating the amount of the dye adsorbed to the porous oxide semiconductor layer on the basis of the thus obtained parameter for dye adsorption quantity.

17 Claims, 11 Drawing Sheets

(56) References Cited

OTHER PUBLICATIONS

Chengwu Shi, Songyuan Dai, Kongjia Wang, Xu Pana, Fantai Kong, Linhua Hu, "The adsorption of 4-tert-butylpyridine on the nanocrystalline TiO2 and Raman spectra of dye-sensitized solar cells in situ", Vibrational Spectroscopy 39 (2005) 99-105.*

Rong Zhang, "Zinc Oxide Thin Films for Dye-Sensitized Solar Cell Applications", (2007), A Thesis, Submitted to the Faculty of Miami University in partial fulfillment of the requirements for the degree of Masters of Science Department of Paper and Chemical Engineering, Miami University, Oxford, Ohio.*

Helena Greijer, Jan Lindgren, and Anders Hagfeldt, Resonance Raman Scattering of a Dye-Sensitized Solar Cell: Mechanism of Thiocyanato Ligand Exchange, J. Phys. Chem. B (2001), 105, 6314-6320.*

Likodimos, V. et al., "Prolonged Light and Thermal Stress Effects on Industrial Dye-Sensitized Solar Cells: A Micro-Raman Investigation on the Long-Term Stability of Aged Cells", J. Phys. Chem. C, 2009, 113, pp. 9412-9422, America Chemical Society, Published on Web.

* cited by examiner

METHOD FOR EVALUATION OF OXIDE SEMICONDUCTOR ELECTRODE, APPARATUS FOR EVALUATION OF OXIDE SEMICONDUCTOR ELECTRODE, AND APPARATUS FOR PRODUCTION OF OXIDE SEMICONDUCTOR ELECTRODE

BACKGROUND

The present technology relates to a method for evaluation of an oxide semiconductor electrode, an apparatus for evaluation of an oxide semiconductor electrode, and an apparatus for production of an oxide semiconductor electrode. More particularly, the present technology relates to a method for evaluation of an oxide semiconductor electrode, an apparatus for evaluation of an oxide semiconductor electrode, and an apparatus for production of an oxide semiconductor electrode, the oxide semiconductor electrode being intended for use in a dye-sensitized solar cell.

Dye-sensitized solar cells are now under intensive research and development owing to their characteristic property that they employ an electrolytic solution, they are produced from cheap raw materials at a low production cost, and they utilize a dye which serves for decoration. An ordinary dye-sensitized solar cell is composed of a substrate with a conductive film formed thereon, an oxide semiconductor electrode formed on the substrate from an oxide semiconductor film (such as $TiO_2$ film) and a dye in combination, an electron transporting material such as iodine, and a counter electrode.

The dye-sensitized solar cell contains a dye (derived from ruthenium complex, for example) which effectively absorbs visible light. Upon light absorption, the dye in excited state injects electrons into the conduction band of $TiO_2$. The electrons injected into $TiO_2$ reach the cathode through the anode and the external circuit. On the other hand, the dye which has donated electrons to $TiO_2$ and is in an oxidized state receives electrons from $I^-$ in the electrolytic solution and then returns to a neutral molecule. In this step, $I^-$ changes into $I_3^-$. The $I_3^-$ receives electrons coming from the counter electrode through the external circuit and then returns to $I^-$. The foregoing cycles are repeated for photoelectric conversion.

The oxide semiconductor electrode is usually a thin film of $TiO_2$ which is formed on the substrate having a conductive film formed thereon. To form the thin film of $TiO_2$, the substrate is coated with a paste of $TiO_2$ particles of nano size, followed by baking at about 450° C. The resulting $TiO_2$ film abounds with pores of nano size, and the interstices of pores adsorb the dye of ruthenium complex. The adsorption of the dye is accomplished by immersion of the $TiO_2$ film in a dye solution.

The dye adsorbed to the oxide semiconductor electrode affects the characteristic properties of the dye-sensitized solar cell differently depending on its amount. The amount of the dye adsorbed to the oxide semiconductor electrode is determined by desorption of the dye in an alkaline solution, followed by colorimetry, as disclosed in Japanese Patent Laid-open No. 2004-79610 (hereinafter referred to as Patent Document 1).

SUMMARY

Unfortunately, the method disclosed in Patent Document 1 needs a time-consuming laborious pretreatment (such as dissolution of the adsorbed dye in an alkaline solution) prior to determination of the dye adsorbed to the oxide semiconductor electrode.

The present disclosure, which was completed in view of the foregoing, is intended to provide a method for evaluation of an oxide semiconductor electrode and an apparatus for evaluation of an oxide semiconductor electrode, the method and apparatus being able to determine rapidly in a simple manner the amount of the dye adsorbed to the oxide semiconductor electrode. The present disclosure is also intended to provide an apparatus for production of an oxide semiconductor electrode having good characteristic properties.

The present disclosure to tackle the above-mentioned problems involves several modes as follows.

The first mode of the present disclosure resides in a method for evaluation of an oxide semiconductor electrode, the method including: performing Raman spectrometry on a porous oxide semiconductor layer having a dye adsorbed thereto, thereby acquiring a Raman spectrum having a peak attributable to the dye and a peak attributable to the oxide semiconductor; obtaining from the Raman spectrum a parameter for dye adsorption quantity which is defined by the formula below; and estimating the amount of the dye adsorbed to the porous oxide semiconductor layer on the basis of the obtained parameter for dye adsorption quantity.

Parameter for dye adsorption quantity=(Peak intensity attributable to dye)/(Peak intensity attributable to oxide semiconductor)  (Formula)

The second mode of the present disclosure resides in a method for evaluation of an oxide semiconductor electrode, the method including: performing Raman spectrometry with the exciting ray directed to several measurement points on one principal plane (orienting toward the incident light) of the porous oxide semiconductor layer having a dye adsorbed thereto, thereby acquiring Raman spectra each having a peak attributable to the dye and a peak attributable to the oxide semiconductor; obtaining from the Raman spectra parameters for dye adsorption quantity which is defined by the formula below; and estimating the state of the dye adsorbed to the porous oxide semiconductor layer on the basis of the obtained parameters for dye adsorption quantity.

Parameter for dye adsorption quantity=(Peak intensity attributable to dye)/(Peak intensity attributable to oxide semiconductor)  (Formula)

The third mode of the present disclosure resides in a method for evaluation of an oxide semiconductor electrode, the method including: performing mapping with Raman spectrometry on one principal plane (orienting toward the incident light) of a porous oxide semiconductor layer having a dye adsorbed thereto, thereby obtaining a distribution of the parameters for dye adsorption quantity (on the one principal plane) defined by the formula below; and evaluating the state of dye adsorption to the porous oxide semiconductor layer on the basis of the parameters for dye adsorption quantity.

Parameter for dye adsorption quantity=(Peak intensity attributable to dye)/(Peak intensity attributable to oxide semiconductor)  (Formula)

The fourth mode of the present disclosure resides in an apparatus for evaluation of an oxide semiconductor electrode, the apparatus including a Raman spectrometer and an arithmetic processor, the Raman spectrometer performing Raman spectrometry on the central part of one principal plane (orienting toward the incident light) of the oxide semiconductor electrode, the arithmetic processor calculating the parameter for dye adsorption quantity, which is defined by the formula below, from the Raman spectrum obtained by the Raman spectrometer, comparing the thus calculated parameter for dye adsorption quantity with a prescribed threshold value, and regarding the oxide semiconductor electrode as having good characteristic properties in the case where the parameter for dye adsorption quantity exceeds the prescribed threshold value.

Parameter for dye adsorption quantity=(Peak intensity attributable to dye)/(Peak intensity attributable to oxide semiconductor) (Formula)

The fifth mode of the present disclosure resides an apparatus for production of an oxide semiconductor electrode, the apparatus including a Raman spectrometer, an arithmetic processor, a controlling unit, and a dye solution feeder, the Raman spectrometer performing Raman spectrometry on several measurement points on one principal plane (orienting toward the incident light) of the oxide semiconductor electrode, the arithmetic processor calculating the parameter for dye adsorption quantity, which is defined by the formula below, from each of the Raman spectra obtained by the Raman spectrometer, calculating the coefficient of variation defined by (Standard deviation/Average)×100%, the controlling unit comparing the coefficient of variation with a prescribed threshold value, and giving feedback control to the dye solution feeder to control its feeding action.

Parameter for dye adsorption quantity=(Peak intensity attributable to dye)/(Peak intensity attributable to oxide semiconductor) (Formula)

The present disclosure provides a simple and rapid way of determining the amount of the dye adsorbed to the oxide semiconductor electrode. The present disclosure also provides an apparatus for producing an oxide semiconductor electrode with superior characteristic properties.

DETAILED DESCRIPTION OF THE PREFERRED EMBODIMENTS

The embodiments of the present disclosure will be described below with reference to the accompanying drawings. The description develops in the following order.
1. The first embodiment (demonstrating the first example of the method for evaluation of an oxide semiconductor electrode)
2. The second embodiment (demonstrating the second example of the method for evaluation of an oxide semiconductor electrode)
3. The third embodiment (demonstrating the third example of the method for evaluation of an oxide semiconductor electrode)
4. The fourth embodiment (demonstrating the fourth example of the method for evaluation of an oxide semiconductor electrode)
5. The fifth embodiment (demonstrating the method of production of a dye-sensitized solar cell)
6. The sixth embodiment (demonstrating the apparatus for evaluation of an oxide semiconductor electrode)
7. The seventh embodiment (demonstrating the apparatus for production of an oxide semiconductor electrode)
8. Additional embodiments (or modified embodiments)

1. The First Embodiment

Example of the Structure of the Dye-Sensitized Solar Cell

Figure 1:
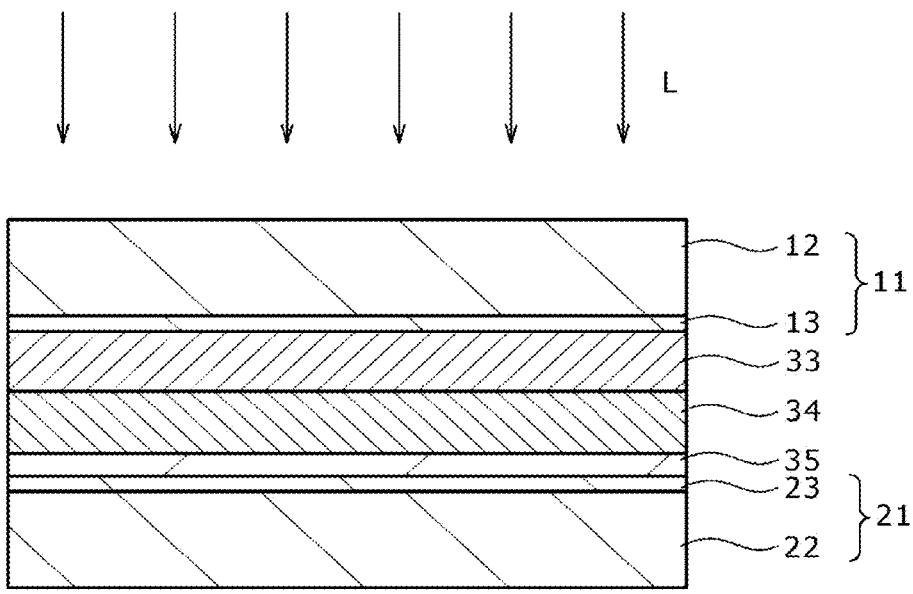
FIG. 1 is a sectional view showing an example of the structure of a dye-sensitized solar cell.

For easy understanding of the present disclosure, this section describes the structure of the dye-sensitized solar cell pertaining to the first embodiment. FIG. 1 is a sectional view showing an example of the structure of the dye-sensitized solar cell. As shown in FIG. 1, this solar cell is composed of a transparent substrate 11 and a counter substrate 21 which support between them an oxide semiconductor electrode layer 33, an electrolyte layer 34, and a counter electrode 35. The transparent substrate 11 is composed of a base plate 12 and a transparent conductive layer 13 which is formed on one principal plane of the base plate 12. On the transparent conductive layer 13 is formed the oxide semiconductor electrode layer 33 containing a dye adsorbed thereto. The counter substrate 21 is composed of a base plate 22 and a transparent conductive layer 23 which is formed on one principal plane of the base plate 22. On the transparent conductive layer 23 is formed the counter electrode 35. The assembly of the transparent substrate 11 and the oxide semiconductor electrode layer 33 formed thereon and the assembly of the counter substrate 21 and the counter electrode 35 formed thereon are joined together, with the electrolyte layer 34 interposed between them. That side of the transparent substrate 11 which is opposite to the plane having the oxide semiconductor electrode layer 33 formed thereon functions as the light receiving plane. In other words, of the two principal planes of the oxide semiconductor electrode layer 33, the principal plane facing the transparent substrate 11 is irradiated with light L. Incidentally, the region held between the transparent substrate 11 and the counter electrode 35 (formed on the counter substrate 21) has its periphery sealed with a sealant (not shown).
(Transparent Substrate)

The transparent substrate 11 is composed of the base plate 12 and the transparent conductive layer 13 which is formed on one principal plane of the base plate 12. Incidentally, the transparent substrate 11 may not need the transparent conductive layer 13 so long as the base plate 12 is transparent and conductive.

(Base Plate)

The base plate 12 is not specifically restricted so long as it is transparent. It may be formed from any transparent inorganic or plastic material. Transparent plastic material is desirable because of its good processability and light weight. The plastic material may be formed into film, sheet, or plate to be used as the base plate 12. In addition, it should preferably be superior in barrier properties (to block moisture and gas), solvent resistance, and weather resistance. Examples of the inorganic material include quartz, sapphire, and glass. The plastic material may be selected from any known ones, such as triacetyl cellulose (TAC), polyester (TPEE), polyethylene terephthalate (PET), polyethylene naphthalate (PEN), polyimide (PI), polyamide (PA), aramide, polyethylene (PE), polyacrylate, polyether sulfone, polysulfone, polypropylene (PP), diacetyl cellulose, polyvinyl chloride, acrylic resin (PMMA), polycarbonate (PC), epoxy resin, urea resin, urethane resin, melamine resin, and cycloolefin polymer (COP). Of these inorganic and plastic materials, the one having a high transmittance in the visible region is desirable (although not essential).

(Transparent Conductive Layer)

The transparent conductive layer 13 is formed from any one of ITO (indium-tin compound oxide), FTO (fluorine-doped $SnO_2$), ATO (antimony-doped $SnO_2$), $SnO_2$, ZnO, and IZO (indium-zinc compound oxide). Its formation into thin film form may be achieved by vapor deposition, sputtering, coating, or the like.

(Counter Substrate)

The counter substrate 21 is composed of the base plate 22 and the transparent conductive layer 23 which is formed on one principal plane of the base plate 22.

(Base Plate)

The base plate 22 need not be transparent but may be opaque. It may be formed from any one of such transparent or opaque inorganic or plastic materials as exemplified above for the base plate 12. Metal is another opaque material.

(Transparent Conductive Layer)

The transparent conductive layer 23 is formed from any one of ITO (indium-tin compound oxide), FTO (fluorine-doped $SnO_2$), ATO (antimony-doped $SnO_2$), $SnO_2$, ZnO, and IZO (indium-zinc compound oxide). Its formation into thin film form may be achieved by vapor deposition, sputtering, coating, or the like.

(Counter Electrode)

The counter electrode 35 may be formed from any conductive material. The one which is formed from an insulating material may be acceptable so long as it has a conductive catalyst layer formed on the plane facing the electrolyte layer 34. The conductive material should preferably be selected from electrochemically stable ones, such as platinum, gold, carbon, and conductive polymer.

(Oxide Semiconductor Electrode Layer)

The oxide semiconductor electrode layer 33 is a thin film of porous oxide semiconductor containing a dye adsorbed thereto. It is formed on the transparent conductive layer 13 by coating and ensuing sintering from oxide semiconductor fine particles such as $TiO_2$, which are composed of primary particles having an average diameter of 1 to 200 nm, preferably 5 to 100 nm. The base of the oxide semiconductor electrode layer 33 should preferably be an n-type semiconductor which works in such a way that photoexcited electrons in the conduction band function as carriers for anode current.

Other candidates than $TiO_2$ for the oxide semiconductor include such metal oxide semiconductors as MgO, ZnO, $WO_3$, $Nb_2O_5$, $TiSrO_3$, and $SnO_2$. Of these candidates, $TiO_2$ of anatase type is preferable. The examples listed above are not exclusive, and any other materials than listed may be used. The oxide semiconductor electrode layer 33 may be formed from oxide semiconductors differing in kind or particle size in combination with one another.

(Dye)

The oxide semiconductor electrode layer 33 is a layer of porous oxide semiconductor which has a dye (capable of sensitization) adsorbed thereto. The dye may be selected from metal complex dyes (such as ruthenium complex dyes, platinum complex dyes, zinc complex dyes, and palladium complex dyes) and organic dyes (such as methine dyes, xanthene dyes, porphyrin dyes, azo dyes, coumarin dyes, and polyene dyes). These dyes may be used in combination with one another.

(Electrolyte Layer)

The electrolyte layer 34 is a layer formed from a solution of at least one species of substance capable of reversible oxidation-reduction reaction which is dissolved in an electrolyte. The oxidation-reduction system includes, for example, halogens (such as $I^-/I_3^-$ and $Br^-/Br_2$), pseudo-halogens (such as quinone/hydroquinone and $SCN^-/(SCN)_2$), and metal ions (such as iron (II) ion/iron (III) ion and copper (I) ion/copper (II) ion). These examples are not exclusive.

The electrolyte for the electrolyte layer 34 may be a liquid one or a solid one. The latter may be a polymeric gel-like one (which is a polymeric substance containing an electrolyte) or an inorganic solid one. Specific and preferable examples include a combination of iodine ($I_2$) and metal iodide or organic iodide, a combination of bromine ($Br_2$) and metal bromide or organic bromide, ion compound (such as ferrocyanate/ferricyanate and ferrocene/ferricynium ion), viologen dye, and hydroquinone/quinone. The metal compound should preferably contain a cation such as Li, Na, K, Mg, Ca, and Cs. The organic compound should preferably contain a cation selected from quaternary ammonium compounds such as tetraalkyl ammonium, pyridinium, and imidazolium. These examples are not exclusive and they may be used in combination with one another. Particularly preferable among the electrolytes listed above is a combination of $I_2$ and an ionic solution of LiI, NaI, imidazolium iodide, or quaternary ammonium iodide. The electrolyte may be incorporated with an additive, such as 4-tert-butylpyridine and carboxylic acid, for improvement in open voltage.

The solvent for the electrolyte may be selected from polar solvents (such as acetonitrile, propylene carbonate, ethylene carbonate, γ-butyrolactone, pyridine, and dimethylacetamide) and room-temperature molten salt (such as methylpropylimidazolium-iodine) and a mixture thereof. Commonly used solvents are water, alcohols, ethers, esters, carbonate esters, lactones, carboxylate esters, phosphate triesters, heterocyclic compounds, nitriles, ketones, amides, nitromethane, halogenated hydrocarbons, dimethylsulfoxide, sulforane, N-methylpyrrolidone, 1,3-dimethylimidazolidinone, 3-methyloxazolidinone, and hydrocarbons. They may be used in combination with one another. The solvent may also be any one of tetraalkyl compounds, pyridinium compounds, and ionic solutions of imidazolium-based quaternary ammonium salt.

The electrolyte layer 34 may optionally be incorporated with a supporting electrolyte selected from inorganic salts (such as lithium iodide and sodium iodide) and molten salts of imidazolium or quaternary ammonium.

(Action of the Dye-Sensitized Solar Cell)

The dye-sensitized solar cell works in the way explained below. The solar cell receives light L incident onto the receiving surface of the transparent substrate 11. The received light passes through the transparent substrate 11 and impinges on the oxide semiconductor electrode layer 33. The incident light excites the sensitizing dye adsorbed to the oxide semiconductor electrode layer 33, thereby releasing electrons. The released electrons rapidly transfer from the sensitizing dye to the metal oxide fine particles of the oxide semiconductor electrode layer 33. On the other hand, the sensitizing dye which has lost electrons receives electrons from the ions of the electrolyte layer 34, and the molecules which have transferred electrons receive electrons again on the surface of the counter electrode 35. These consecutive reactions generate an electromotive force between the transparent substrate 11 (which is electrically connected with the oxide semiconductor electrode layer 33) and the counter electrode 35. This is the way in which photoelectric conversion takes place.

[Method for Evaluation of the Electrode]

The following is a description of the method for evaluation of the oxide semiconductor electrode pertaining to the first embodiment of the present disclosure. The oxide semiconductor electrode is the one constituting the dye-sensitized solar cell mentioned above.

According to the first embodiment of the present disclosure, the method for evaluation of the oxide semiconductor electrode mainly includes: performing Raman spectrometry on the oxide semiconductor electrode layer 33, thereby acquiring a Raman spectrum; calculating from the Raman spectrum a parameter for dye absorption quantity; and estimating the quantity of the dye adsorbed to the oxide semiconductor electrode layer 33 on the basis of the parameter for dye absorption quantity. Each step will be described below in more detail.

<Raman Spectrometry>

The Raman spectrometry is performed on the central part of one principal plane (orienting toward the incident light) of the oxide semiconductor electrode layer 33. The Raman spectrometry performed in this manner gives a Raman spectrum having a peak attributable to the dye and a peak attributable to the oxide semiconductor. Specifically, the Raman spectrometry is performed as follows. An exciting ray is directed to one principal plane (orienting toward the incident light) of the oxide semiconductor electrode layer 33 through the transparent substrate 11. The exciting ray causes Raman scattered light to be released from the oxide semiconductor electrode layer 33. The Raman scattered light is detected as a Raman spectrum having a peak attributable to the dye and a peak attributable to the oxide semiconductor. The range of wave length to be measured is established such that one spectrum has a peak attributable to the dye and a peak attributable to the oxide semiconductor.

Figure 2:
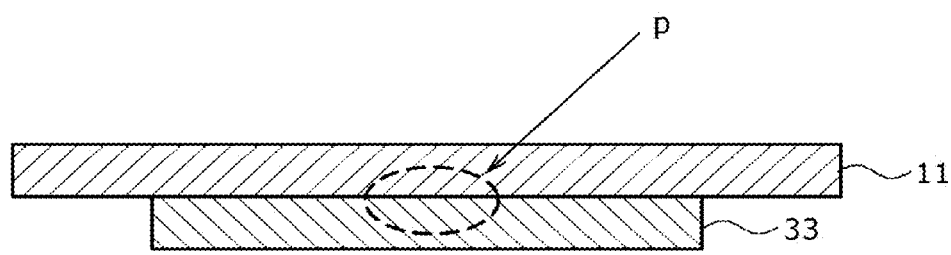
FIG. 2 is a sectional view showing an example of the structure of a specimen for measurement.

The Raman spectrometry is performed typically in the course of production of the dye-sensitized solar cell. Specifically, it is performed during or after the step of dye adsorption that follows the step of forming the oxide semiconductor electrode layer 33 on the transparent substrate 11. Therefore, the specimen for measurement is composed of the transparent substrate 11 and the oxide semiconductor electrode layer 33 formed thereon, as shown in FIG. 2. The exciting ray for Raman spectrometry is directed to the central part of one principal plane (orienting toward incident light) of the oxide semiconductor electrode layer 33 as pointed by arrow p. The Raman spectrometry offers the advantage of being capable of determination in a short time without touching and destroying the specimen.

<Calculation of Parameter for Dye Adsorption Quantity>

The resulting Raman spectrum is examined to calculate the peak intensity attributable to the dye and the peak intensity attributable to the oxide semiconductor. The peak intensity should preferably be expressed in terms of peak area obtained by curve fitting in order to avoid the effect of noise in the spectrum. The next step is to calculate the ratio of the peak intensity attributable to the dye to the peak intensity attributable to the oxide semiconductor. The thus calculated ratio is the parameter for dye adsorption quantity (defined by the formula below) that represents the central part of one principal plane (orienting toward the incident light) of the oxide semiconductor electrode layer 33.

[Parameter for dye adsorption quantity]=[Peak intensity attributable to dye]/[Peak intensity attributable to oxide semiconductor]  (Formula)

(Atmosphere for Raman Spectrometry)

The Raman spectrometry should be carried out in an atmosphere of low humidity (with a dew point lower than −20° C.). Moreover, in the case where a laser beam is used for excitation, it should be so controlled as to have the minimal irradiation density. Measurement in a high-humidity atmosphere, in which the laser beam is affected by water vapor, will give a low value for the peak intensity attributable to the dye adsorbed to the oxide semiconductor electrode layer 33. This trouble can be avoided by keeping dry the atmosphere for measurement and setting low the irradiation density of the laser beam. The foregoing method permits reproducible determination of the dye adsorbed to the oxide semiconductor electrode layer 33.

(Wave Length of Exciting Ray for Raman Spectrometry)

The Raman spectrometry for the oxide semiconductor electrode layer 33 is accompanied by the dye's fluorescence induced by irradiation with the exciting ray in the case of specific dyes. This fluorescence is detrimental to Raman spectrometry. Therefore, the exciting ray should have a wave length longer than 1000 nm, preferably that in the infrared region. The exciting ray with such a specific wave length permits determination of the dye of varied types adsorbed to the oxide semiconductor electrode layer 33.

On the other hand, for highly sensitive determination of the dye adsorbed to the oxide semiconductor electrode layer 33, it is desirable to use the exciting ray of wave length (say, about 500 nm) within a specific range.

<Estimation of the Quantity of the Adsorbed Dye>

In the next step, the quantity of the dye adsorbed to the oxide semiconductor electrode layer 33 is estimated on the basis of the parameter for dye adsorption quantity which has been obtained from the result of Raman spectrometry with the exciting ray directed to the central part of one principal plane (orienting toward the incident light) of the oxide semiconductor electrode layer 33. This parameter correlates to the quantity of the dye adsorbed to the oxide semiconductor electrode layer 33. Consequently, it makes it possible to determine the quantity of the dye adsorbed to the oxide semiconductor electrode layer 33.

The Raman spectrometry involves difficulties in determination of the dye (as a simple substance) from its spectrum intensity because it is subject to change in sensitivity depending on the state of the specimen and the environment of measurement. This is not the case for the Raman spectrometry performed on the oxide semiconductor electrode layer 33, because its determination is based on the parameter for dye adsorption quantity (or the ratio of the peak intensity attributable to the dye to the peak intensity attributable to the oxide semiconductor). Raman spectrometry in this manner permits reproducible determination of the dye adsorbed to the oxide semiconductor electrode layer 33 without being affected by the state of the specimen and the environment of measurement.

(Saturation with Adsorbed Dye)

Determination of the dye adsorbed to the oxide semiconductor electrode layer 33 on the basis of the parameter for dye adsorption quantity which is obtained from the result of Raman spectrometry with the exciting ray directed to the central part of one principal plane (orienting toward the incident light) of the oxide semiconductor electrode layer 33 permits one to detect whether or not the quantity of the dye adsorbed to the oxide semiconductor electrode layer 33 has reached saturation.

The oxide semiconductor electrode layer 33 saturated with the dye adsorbed thereto helps the dye-sensitized solar cell provided with it to generate electricity efficiently. Consequently, it is regarded as a superior oxide semiconductor electrode.

Dye adsorption may be accomplished by immersing a member composed of the transparent substrate 11 and the oxide semiconductor electrode layer 33 formed thereon in a dye solution. In this case, dye adsorption proceeds in the oxide semiconductor electrode layer 33 from its side not in contact with the transparent substrate 11 to its side in contact with the transparent substrate 11, and dye adsorption is finally completed at the central part of one principal plane (orienting toward the incident light) of the oxide semiconductor electrode layer 33 which is in contact with the transparent substrate 11. Therefore, it is possible to surely detect that the oxide semiconductor electrode layer 33 is saturated with the dye adsorbed thereto if the quantity of the dye adsorbed to the oxide semiconductor electrode layer 33 is determined on the basis of the parameter for dye adsorption quantity which is obtained from the result of Raman spectrometry with the exciting ray directed to the central part of one principal plane (orienting toward the incident light) of the oxide semiconductor electrode layer 33 where dye adsorption takes place last.

The state in which the oxide semiconductor electrode layer 33 is saturated with the dye adsorbed thereto may be defined as the one in which the parameter for dye adsorption quantity does not increase with time of dye adsorption any longer during the process for dye adsorption (such as immersion and dropping). Specifically, in the case of immersion process for adsorption, the parameter for dye adsorption quantity is plotted against the duration of dye adsorption, and the region in which the parameter for dye adsorption quantity remains unchanged (or the graph remains flat) is defined as the state in which the oxide semiconductor electrode layer 33 is saturated with the dye adsorbed thereto.

2. The Second Embodiment

According to the second embodiment of the present disclosure, the oxide semiconductor electrode used for the dye-sensitized solar cell mentioned above is evaluated in the following manner. The method for evaluation of the oxide semiconductor electrode includes mainly a step of setting up the threshold value of saturation for the parameter for dye adsorption quantity and a step of comparing the parameter for dye adsorption quantity with the threshold value, thereby determining whether or not the oxide semiconductor electrode is saturated with the dye adsorbed thereto. Each step will be described below in more detail.

<Setting of the Threshold Value of Saturation for the Parameter for Dye Adsorption Quantity>

The first step starts with setting up the threshold value of saturation for the parameter for dye adsorption quantity corresponding to the state in which the oxide semiconductor electrode layer 33 is saturated with the dye adsorbed thereto. The threshold value of saturation for the parameter for dye adsorption quantity may be set up in the following manner.

In the course of dye adsorbing process, the parameter for dye adsorption quantity is measured at the central part of one principal plane (orienting toward the incident light) of the oxide semiconductor electrode layer 33. At the same time, the solar cell provided with the oxide semiconductor electrode layer 33 is examined for the efficiency of power generation. These steps are carried out under several conditions which are expected to include one condition under which the oxide semiconductor electrode layer 33 is saturated with the dye adsorbed thereto.

Figure 3:
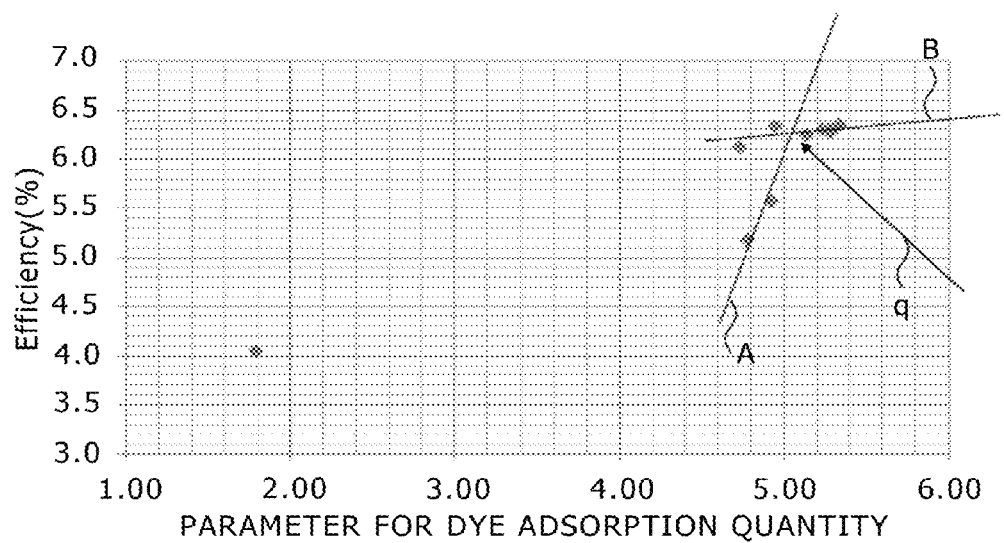
FIG. 3 is a graph in which the efficiency of power generation is plotted against the parameters for dye adsorption quantity.

Then, the efficiency of power generation is plotted against each parameter for dye adsorption quantity. FIG. 3 is a graph in which the efficiency of power generation is plotted against each parameter for dye adsorption quantity. In this graph, several plotted points are classified into two groups, which are denoted by the differently sloped straight lines A and B, respectively. These lines intersect with each other at the point indicated by the arrow q. This intersection (at which the two lines change in slope angle) is defined as the threshold value of saturation of the parameter for dye adsorption quantity.

<Evaluation by Comparison Between the Parameter for Dye Adsorption Quantity and the Threshold Value of Saturation>

If the oxide semiconductor electrode is produced on the basis of the threshold value of saturation for the parameter for dye adsorption quantity (which has been obtained as mentioned above) from the same material under the same condition as used for setting up the threshold value of saturation, it is possible to detect the state in which the oxide semiconductor electrode layer 33 is saturated with the dye adsorbed thereto. For example, the following method may be employed to detect the state in which the oxide semiconductor electrode layer 33 is saturated with the dye adsorbed thereto.

First, the Raman spectrometry is performed on the central part of one principal plane (orienting toward the incident light) of the oxide semiconductor electrode layer 33, so that a Raman spectrum is obtained. Then, the parameter for dye adsorption quantity is obtained from this Raman spectrum. The thus obtained parameter for dye adsorption quantity is examined to see whether or not it is higher than the threshold value of saturation. If it is found that the parameter for dye adsorption quantity is higher than the threshold value of saturation, it is determined that the oxide semiconductor electrode layer 33 is saturated with the dye adsorbed thereto. If it is found that the parameter for dye adsorption quantity is lower than the threshold value of saturation, it is determined that the oxide semiconductor electrode layer 33 is not saturated with the dye adsorbed thereto.

3. The Third Embodiment

According to the third embodiment of the present disclosure, the oxide semiconductor electrode used for the dye-sensitized solar cell mentioned above is evaluated in the following manner. The method for evaluation of the oxide semiconductor electrode mainly includes a step of performing Raman spectrometry at several points on one principal plane (orienting toward the incident light) of the oxide semiconductor electrode layer 33, thereby obtaining the parameter for dye adsorption quantity at individual measurement points, and a step of evaluating the state of dye adsorption on the basis of the parameter for dye adsorption quantity obtained from individual measurement points. Each step will be described below in more detail.

<Acquisition of the Parameter for Dye Adsorption Quantity at Individual Measurement Points>

First, Raman spectrometry is performed on several measurement points on one principal plane (orienting toward the incident light) of the oxide semiconductor electrode layer 33 so as to obtain Raman spectra for individual measurement points. Each Raman spectrum is examined for the peak intensity attributable to the dye and the peak intensity attributable to the oxide semiconductor, so as to calculate the parameter for dye adsorption quantity which is defined as [peak intensity attributable to the dye] divided by [peak intensity attributable to the oxide semiconductor].

To be specific, the measurement points are assigned on one principal plane (orienting toward the incident light) of the oxide semiconductor electrode layer 33 as follows. The first point is at the center of the principal plane. The second and third points are at the intersections of the straight line passing through the center and the peripheral ends of the principal plane. The fourth and higher points are on the above-mentioned straight line (except for the first, second, and third points). Incidentally, the measurement points may be limited to three (one at the center and two at the peripheral ends of the principal plane).

Figure 4:
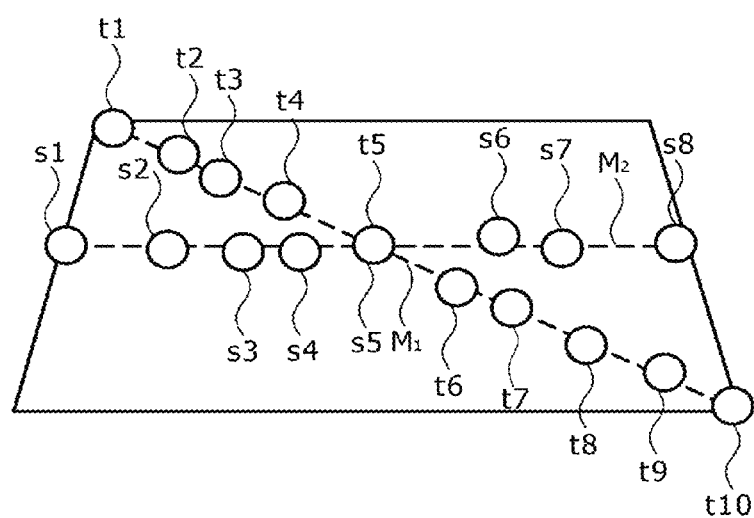
FIG. 4 is a schematic diagram showing an example of the points of measurement.

FIG. 4 specifically indicates ten measurement points on one principal plane (orienting toward the incident light) of the oxide semiconductor electrode layer 33. One point (t5) at the center of the principal plane. Two points (t1 and t10) at the intersections of the straight line $M_1$ passing through the point (t5) at the center and the peripheral edge of the principal plane. Seven points (t2, t3, t4, t6, t7, t8, t9) on the straight line $M_1$. The number of measurement points may be increased or decreased so long as there are three (one at the center and two at the peripheral edges), although it should preferably be at least 10 for accurate evaluation.

The measurement points may also be arranged at different positions than mentioned above. For example, one point (s5) at the center of one principal plane (orienting toward the incident light) of the oxide semiconductor electrode layer 33; two points (s1, s8) at the intersections of the straight line $M_2$ passing through the center (s5) and the peripheral edges of the principal plane; and additional five points (s2, s3, 34, s6, s7) on the straight line $M_2$. The number of measurement points may be increased or decreased so long as there are three (one at the center and two at the peripheral edges), although it should preferably be at least 10 for accurate evaluation.

Another example of the arrangement of the measurement points is as follows. One point (t5) at the center of the principal plan; two points (t1, t10) at the intersections of the straight line $M_1$ passing through the center (t5) and the peripheral edges of the principal plane; additional seven points (t2, t3, t4, t6, t7, t8, t9) on the straight line $M_1$; two points (s1, s8) at the intersections of the straight line $M_2$ passing through the center (s5) and the peripheral edges of the principal plane; and additional five points (s2, s3, s4, s6, s7). All the measurement points count 17.

The Raman spectrum obtained from each measurement point is used to calculate the parameter for dye adsorption quantity.

<Evaluation of the State of Dye Adsorption to the Oxide Semiconductor Electrode Layer>

The state of dye adsorption to the oxide semiconductor electrode layer is evaluated in the following manner on the basis of the dispersion of the parameters for dye adsorption quantity which have been determined at several measurement points. First, the parameters for dye adsorption quantity which have been determined at several measurement points are processed to obtain their average value and standard deviation. Next, the parameters for dye adsorption quantity which have been determined at several measurement points are processed to obtain the coefficient of variation, which is defined as (Average/Standard deviation)×100%. The coefficient of variation lower than the prescribed threshold value suggests that the quantity of the dye adsorbed to the oxide semiconductor electrode layer 33 has reached saturation and the dye has been evenly adsorbed to the oxide semiconductor electrode layer 33 and that the oxide semiconductor electrode has a good efficiency of power generation. On the other hand, the coefficient of variation higher than the prescribed threshold value suggests that the quantity of the dye adsorbed to the oxide semiconductor electrode layer 33 has not yet reached saturation and the dye is not evenly adsorbed to the oxide semiconductor electrode layer 33 and that the oxide semiconductor electrode does not have a good efficiency of power generation. Typically, the prescribed threshold value is set 5% or lower.

4. The Fourth Embodiment

According to the fourth embodiment of the present disclosure, the oxide semiconductor electrode used for the dye-sensitized solar cell mentioned above is evaluated by means of the distribution of the parameters for dye adsorption quantity which is obtained from Raman mapping on one principal plane (orienting toward the incident light) of the oxide semiconductor electrode layer 33.

The distribution of the parameters for dye adsorption quantity is obtained as follows. One principal plane (orienting toward the incident light) of the oxide semiconductor electrode layer 33 is sequentially scanned with an exciting laser beam, so that Raman spectra are obtained from the regularly spaced measurement points. The thus obtained Raman spectra are used for calculation of the parameters for dye adsorption quantity. In this way there is obtained the distribution of the parameters for dye adsorption quantity on one principal plane (orienting toward the incident light) of the oxide semiconductor electrode layer 33.

The thus obtained distribution of the parameters for dye adsorption quantity is output in the form of an image with colors differing in gradation or saturation according to the magnitude of the parameters. This image permits one to visually recognize the distribution of the parameters for dye adsorption quantity on one principal plane (orienting toward the incident light) of the oxide semiconductor electrode layer 33. Thus, the image representing the distribution of the parameters for dye adsorption density permits one to confirm the amount and state of dye adsorption to the oxide semiconductor electrode layer 33. In the case of an image with colors varying in gradation depending on the magnitude of the parameters for dye adsorption quantity, colors with dense and uniform gradation suggest that adsorption of the dye to the oxide semiconductor electrode layer 33 is uniform and saturated.

5. The Fifth Embodiment

The fifth embodiment of the present disclosure demonstrates the method for producing the dye-sensitized solar cell while evaluating the oxide semiconductor electrode as explained above in the first to fourth embodiments. The following is a description of the fifth embodiment which demonstrates the method for production of the dye-sensitized solar cell. The method according to the fifth embodiment involves the evaluation of the oxide semiconductor electrode which is carried out during production as explained above in the first to fourth embodiments.

<Method for Production of the Dye-Sensitized Solar Cell>

First, the transparent base plate 12 is coated with the transparent conductive layer 13. Thus there is obtained the transparent substrate 11. Then, the transparent conductive layer 13 is coated with a paste of oxide semiconductor fine particles, followed by sintering. Thus there is obtained the porous oxide semiconductor electrode layer composed of oxide semiconductor fine particles. The porous oxide semiconductor electrode layer is immersed in a dye-containing solution. Thus there is obtained the oxide semiconductor electrode layer 33 composed of the semiconductor fine particles and the dye adsorbed thereto. In this step, the method for evaluation of the oxide semiconductor electrode, which pertains to any of the first to fourth embodiments mentioned above, is employed to confirm the amount of the dye adsorbed to the oxide semiconductor electrode layer 33 or the amount and the adsorption state of the dye adsorbed to the oxide semiconductor electrode layer 33. Thus there is obtained the oxide semiconductor electrode layer 33 which is regarded as having good characteristic properties.

After the step for dye adsorption, the transparent substrate 11 having the oxide semiconductor electrode layer 33 with the dye adsorbed thereto is placed opposite to the counter substrate 21 having the counter electrode 35 formed thereon, with a space left between them. This space is filled with an electrolyte. Thus there is obtained the electrolyte layer 34. The foregoing steps yield the dye-sensitized solar cell as desired.

6. The Sixth Embodiment

Structure of the Apparatus for Evaluation

Figure 5:
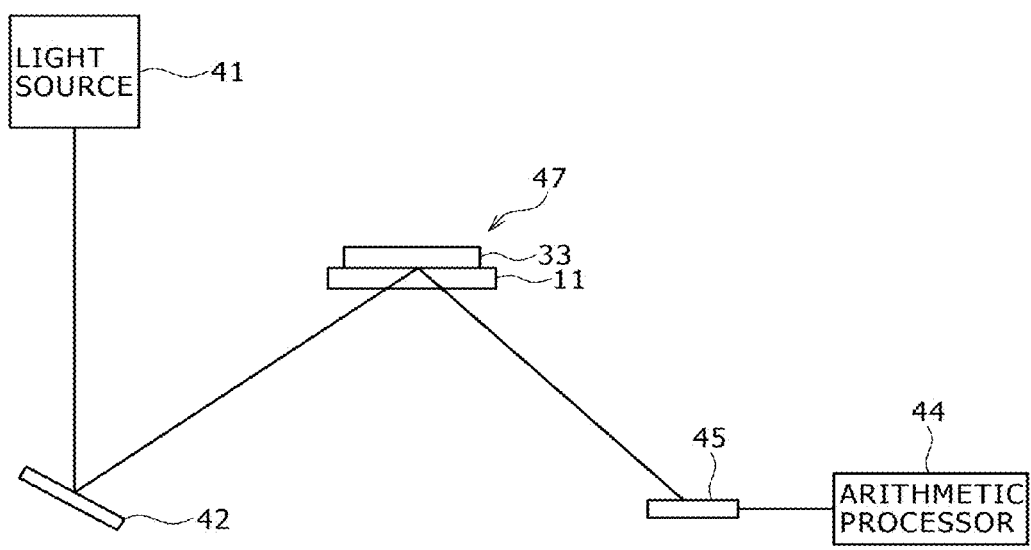
FIG. 5 is a schematic diagram showing an example of the structure of the apparatus for evaluation of an oxide semiconductor electrode.

The sixth embodiment relates to the apparatus (explained below) for evaluation of the oxide semiconductor electrode. This apparatus is constructed as schematically shown in FIG. 5. It is composed of a light source 41, a mirror 42, a detector 45, and an arithmetic processor 44. The light source 41 directs the exciting ray to a specimen 47, and the detector 45 detects Raman scattered light from the specimen 47. The arithmetic processor 44 calculates the parameter for dye adsorption quantity from the Raman spectrum detected by the detector 45. The specimen is a member composed of the oxide semiconductor electrode layer 33 and the transparent substrate 11 as shown in FIG. 2.

The light source 41 emits the exciting ray (such as laser beam) with a prescribed wave length. In other words, the light source 41 is a laser source (such as gas laser and semiconductor laser) that emits a laser beam of specific wave length. The light source 41 has as many laser sources as necessary according to the wave lengths prescribed. The specimen 47 is irradiated with the exciting ray which is emitted from the light source 41 and deflected by the mirror 42 toward the specimen.

The detector 45 is composed of a light dividing section for dividing the Raman scattered light according to wave lengths and a light detecting section for detecting the separated Raman scattered light according to wave lengths. The light dividing section may be a diffraction grating, for example. The light detecting section may be a single-channel detector that detects the component of specific wave length from the Raman scattered light separated by the light dividing section. Alternatively, it may be a multi-channel detector that simultaneously detects several channels of different wave lengths from the Raman scattered light separated by the light dividing section. Such light detecting section includes a photomultiplier tube and CCD (Charge Coupled Device).

The arithmetic processor 44 may be a computer, such as ordinary personal computer (PC), which is composed of a CPU (Central Processing Unit), a ROM (Read Only Memory) that stores program to control the CPU's operation, and a RAM (Random Access Memory), and is capable of arithmetic processing according to the program's instructions.

The apparatus for evaluation may also be provided with a specimen chamber (not shown) capable of temperature and humidity control for the specimen 47 held therein. The atmosphere in the specimen chamber should be kept low in humidity so as to prevent the peak intensity (attributable to the dye adsorbed to the oxide semiconductor electrode layer 33) from decreasing due to moisture.

<Action of the Apparatus for Evaluation>

Figure 6:
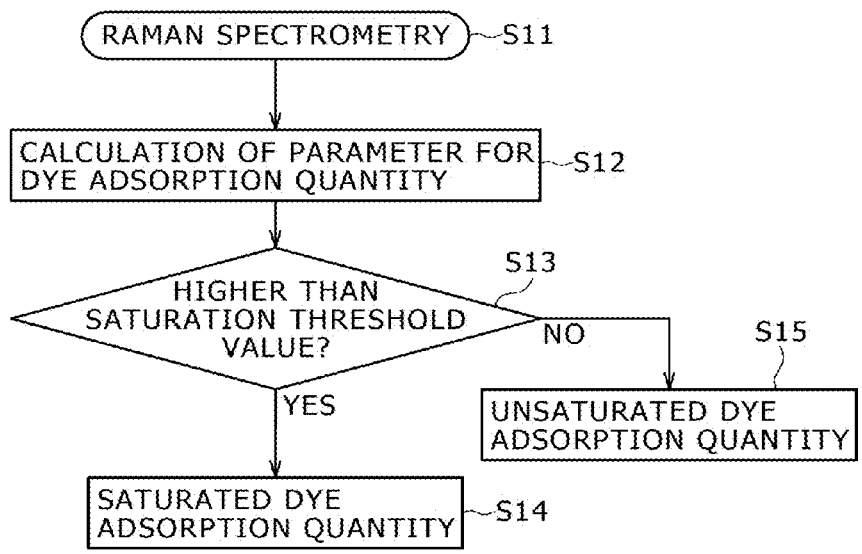
FIG. 6 is a flow chart illustrating the action of the apparatus for evaluation of oxide semiconductor electrodes.

The apparatus for evaluation of the oxide semiconductor electrode works in the way as explained below according to the flow chart shown in FIG. 6. In Step S11, Raman spectrometry is performed on the oxide semiconductor electrode layer 33, with the exciting ray directed to the central part of its one side orienting toward the incident light, and the resulting Raman spectrum is detected by the detector 45. In Step S12, the arithmetic processor 44 calculates the parameter for dye adsorption quantity from the Raman spectrum received from the detector 45. In Step S13, the arithmetic processor 44 determines whether or not the parameter for dye adsorption quantity is higher than the threshold value for saturation. Incidentally, the threshold value for saturation is established in the same way as in the second embodiment, and it is set in the arithmetic processor 44. If the arithmetic processor 44 determines that the parameter of dye absorption quantity is higher than the threshold value for saturation, Step S13 proceeds to Step S14 in which a determination is made on that the oxide semiconductor electrode layer 33 is saturated with the dye adsorbed thereto. If the arithmetic processor 44 determines that the parameter for dye absorption quantity is lower than the threshold value for saturation, Step S13 proceeds to Step S15 in which a determination is made on that the oxide semiconductor electrode layer 33 is not yet saturated with the dye adsorbed thereto.

Figure 7:
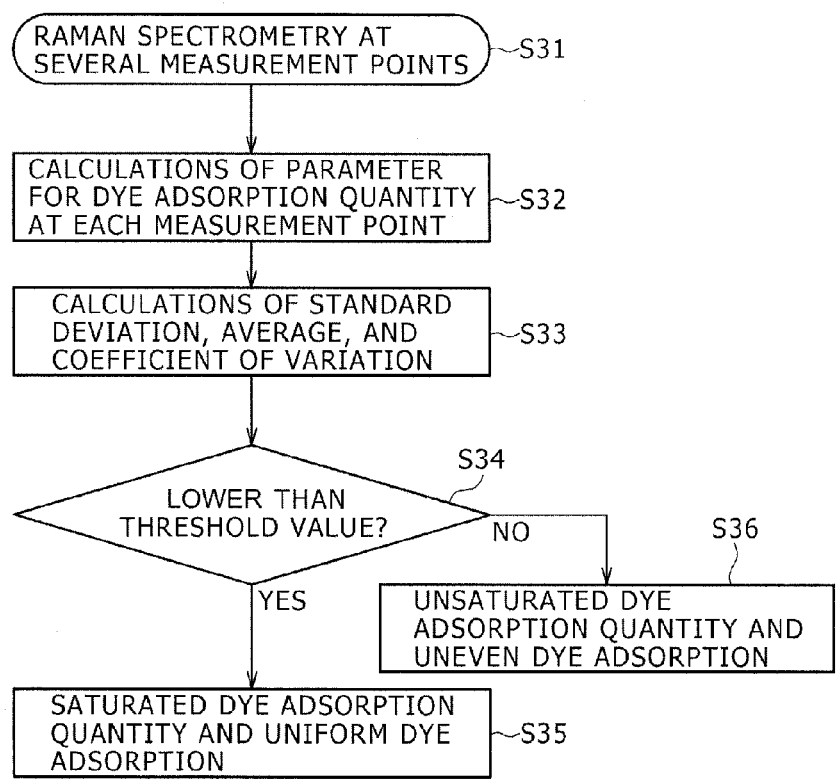
FIG. 7 is a flow chart illustrating the action of the apparatus for evaluation of oxide semiconductor electrodes.

The apparatus for evaluation of the oxide semiconductor electrode works in another way as explained below according to the flow chart shown in FIG. 7. In Step S31, Raman spectrometry is performed on the oxide semiconductor electrode layer 33, with the exciting ray directed to several measurement points on its one side orienting toward the incident light, and the resulting Raman spectra are detected by the detector 45. As in the third embodiment, the measurement points, which are on one principal plane (orienting toward the incident light) of the oxide semiconductor electrode layer 33, may be assigned to one point at the center, two points at the intersections of the straight line passing through the center and the peripheral edges, and additional several points on the straight line other than the three points mentioned above.

In Step S32, the arithmetic processor 44 calculates the parameter for dye adsorption quantity from the Raman spectra obtained from the individual measurement points. In Step S33, the arithmetic processor 44 also calculates the average value and standard deviation of the parameters for dye adsorption quantity obtained from the individual measurement points and further calculates the coefficient of variation ([Standard deviation/Average]×100%) which denotes the variation of the parameters for dye adsorption quantity at the individual measurement points. In Step S34, the arithmetic processor 44 compares the coefficient of variation with the prescribed threshold value. If the arithmetic processor 44 determines that the coefficient of variation is lower than the prescribed threshold value, Step S34 proceeds to Step S35 in which the arithmetic processor 44 determines that the oxide semiconductor electrode layer 33 is saturated with the dye adsorbed thereto and the dye is uniformly adsorbed to the oxide semiconductor electrode layer 33 and the oxide semiconductor has an adequate efficiency of power generation. On the other hand, if the arithmetic processor 44 determines that the standard deviation exceeds the prescribed threshold value, Step S34 proceeds to Step S36, in which the arithmetic processor 44 estimates that the oxide semiconductor electrode layer 33 is not yet saturated with the dye adsorbed thereto, the dye is not adsorbed uniformly to the oxide semiconductor electrode layer 33, and the oxide semiconductor electrode does not have an adequate efficiency of power generation. The threshold value is set up typically at 5%.

7. The Seventh Embodiment

Construction of the Production Unit

Figure 8:
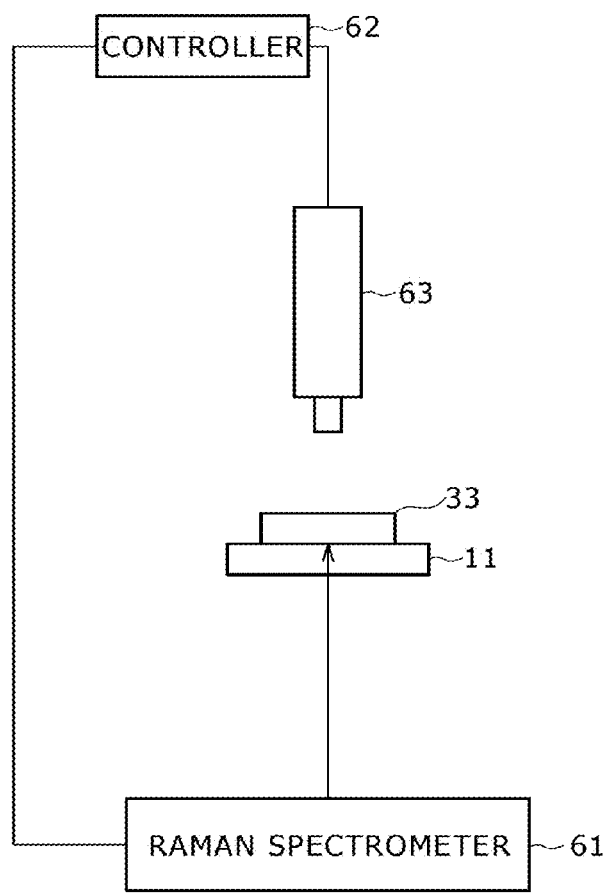
FIG. 8 is a schematic diagram showing an example of the structure of the apparatus for production of oxide semiconductor electrodes.

The seventh embodiment relates to an apparatus for production of the oxide semiconductor electrode. The apparatus is constructed as schematically shown in FIG. 8 and explained in the following. It is composed of a Raman spectrometer 61, a controller 62, and a dye solution feeder 63. The Raman spectrometer 61 is the same one as used for evaluation of the oxide semiconductor electrode in the sixth embodiment. It is designed to perform Raman spectrometry to obtain Raman spectra, calculate the parameters for dye adsorption quantity from the thus obtained Raman spectra, and perform statistical processing on the thus calculated parameters for dye adsorption quantity. The dye solution feeder 63 is a dispenser of various type (such as ink jet system) to feed a dye solution. The controller 62 performs feed-back control over the dye solution feeder 63 for its solution supply in response to the result obtained by the Raman spectrometer 61.

<Action of the Production Unit>

The apparatus for production of the oxide semiconductor electrode works in the way explained in the following. First, a member composed of the transparent substrate 11 and the oxide semiconductor electrode layer 33 formed thereon is arranged at a prescribed position. This member undergoes Raman spectrometry by the Raman spectrometer 61 which directs exciting rays to several measurement points on one principal plane (orienting toward the incident light) of the oxide semiconductor electrode layer 33. Then the Raman spectrometer 61 calculates the parameters for dye adsorption quantity at individual measurement points. The measurement points may be identical with those in the third embodiment. That is, they include one point at the center, two points at the intersections of the straight line passing through the center and the peripheral edges, and more than one additional point on the straight line.

The Raman spectrometer 61 calculates the average and standard deviation of the parameters for dye adsorption quantity at individual measurement points and then calculates the coefficient of variation ([Standard deviation/Average value]× 100%) which denotes the variation of the parameters for dye adsorption quantity at individual measurement points. It sends the coefficient of variation to the controller 62. The controller 62 compares the coefficient of variation (received from the Raman spectrometer 61) with the previously established threshold value. The result of comparison is fed back to the dye solution feeder 63 for its feed control. The prescribed threshold value is set up typically at 5%. The apparatus constructed as mentioned above produces the oxide semiconductor electrode layer 33 in which the dye is adsorbed uniformly to saturation and which is capable of efficient electric power generation.

EXAMPLES

Measurement Example 1

A specimen as shown in FIG. 2 was prepared in the following manner. It is composed of the transparent substrate 11, which is an FTO base plate, the oxide semiconductor electrode layer 33, which is a porous $TiO_2$ film, and the ruthenium dye (Z907), which is adsorbed to the porous $TiO_2$ film.

First, the FTO base plate was coated with a paste of $TiO_2$, followed by baking in an electric furnace at 100 to 600° C. Thus there was obtained a porous sintered body of $TiO_2$. Then, it was immersed for a prescribed period of time in a solution of ruthenium dye (Z907) dissolved in a mixture of tert-butanol and acetonitrile, so that the porous sintered body of $TiO_2$ was made to adsorb the sensitizing dye. In this way there was obtained the specimen for measurement as shown in FIG. 2 which is composed of the transparent substrate 11 (or FTO base plate) and the oxide semiconductor electrode layer 33 (or porous $TiO_2$ film) which has adsorbed the dye.

Raman spectrometry was performed on the specimen, with the exciting ray directed to the central point (denoted by the arrow p in FIG. 2) on one principal plane (orienting toward the incident light) of the oxide semiconductor electrode layer 33. In this way there was obtained the Raman spectrum shown in FIG. 9. Incidentally, the Raman spectrometry was carried out under the following conditions.

Light source: DPSS
Wave length: 473 nm
Temperature of atmosphere: 25° C.
Humidity of atmosphere: 20%

Figure 9:
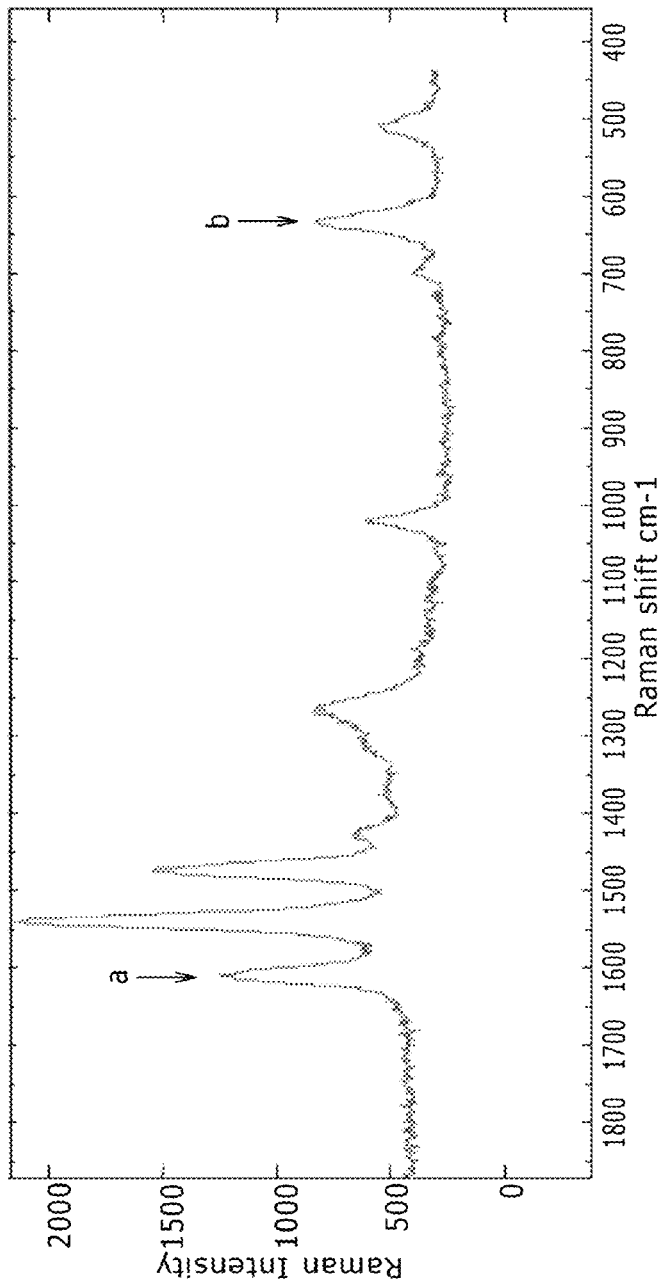
FIG. 9 is a diagram showing a Raman spectrum of an oxide semiconductor electrode.

FIG. 9 shows the Raman spectrum obtained by the Raman spectrometry mentioned above. In this spectrum, the arrow a denotes the peak attributable to the dye, and the arrow b denotes the peak attributable to the oxide semiconductor ($TiO_2$). From this spectrum was calculated the parameter for dye adsorption quantity which is defined by the formula below.

(Parameter for dye adsorption quantity)=(Peak intensity attributable to dye)/(Peak intensity attributable to oxide semiconductor)

(Determination of Dye)

The specimen was immersed in a mixed solvent of tetrabutylammonium and methanol for dissolution of the dye adsorbed to the oxide semiconductor electrode layer 33. The resulting solution was analyzed by absorptiometry to determine the amount of the dye adsorbed to the oxide semiconductor electrode layer 33.

(Confirmation of Correlation Between the Parameter for Dye Adsorption Quantity and the Amount of Dye Adsorbed)

Calculation of the parameters for dye adsorption quantity and determination of the dye dissolved were performed in the same way as above on the same specimen as above and other specimens differing in the amount of adsorbed dye. The resulting parameter for dye adsorption quantity was plotted against the results of determination of the dye dissolved so as to draw a graph (shown in FIG. 10) that shows the correlation between them.

Figure 10:
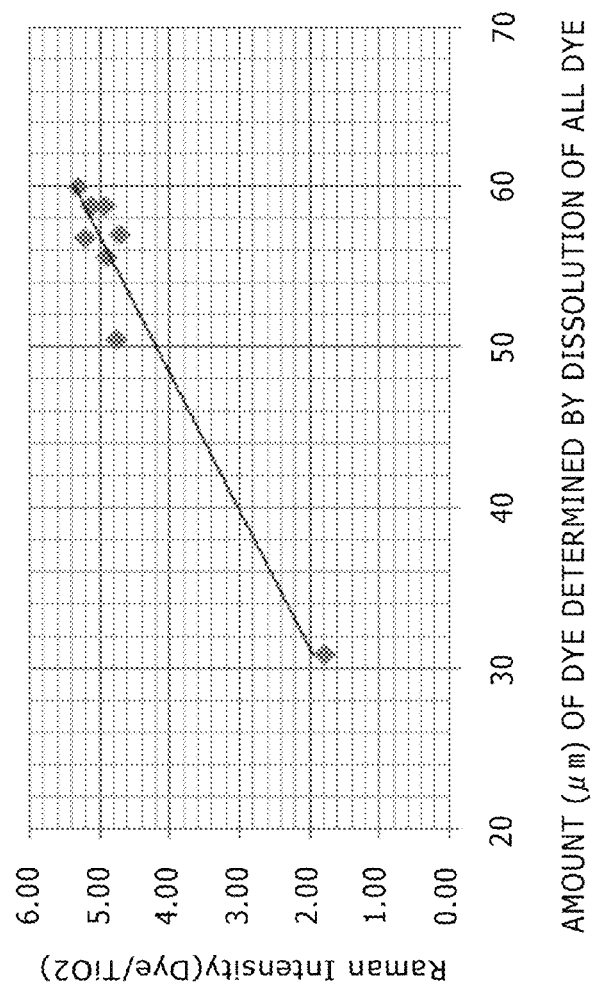
FIG. 10 a graphical representation of a correlation between the quantity of adsorbed dye and the parameter for dye adsorption quantity.

It is noted from FIG. 10 that there is a correlation between the parameter for dye adsorption quantity (which was measured at the center of one principal plane (orienting toward the incident light) of the oxide semiconductor electrode layer 33) and the amount of the dye determined by dissolving all the dye adsorbed. This suggests that it is possible to determine the amount of the dye adsorbed to the oxide semiconductor electrode layer 33 from the parameter for dye adsorption quantity which was measured at the center of one principal plane (orienting toward the incident light) of the oxide semiconductor electrode layer 33.

Measurement Examples 2 and 3

Raman spectrometry was performed in different atmospheres to investigate the effect of atmosphere.

Measurement Example 2

Figure 11:
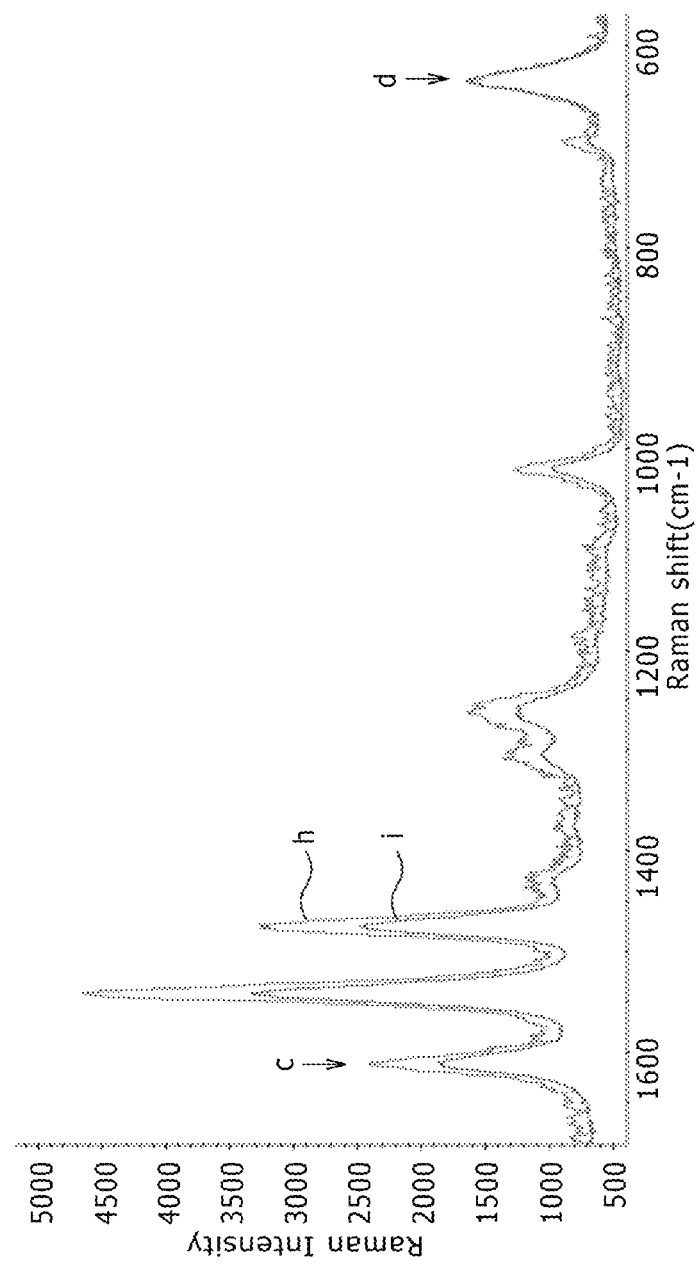
FIG. 11 is a diagram showing Raman spectra obtained under different conditions.

Raman spectrometry was performed on the specimen shown in FIG. 2, which is the same one as in Measurement Example 1, with the exciting ray directed to the central point (denoted by the arrow p) on one principal plane (orienting toward the incident light) of the oxide semiconductor electrode layer 33. In this way there was obtained the Raman spectrum (h) shown in FIG. 11. Incidentally, the Raman spectrometry was carried out under the following conditions.
Light source: DPSS
Wave length: 473 nm
Temperature of atmosphere: 20° C.
Humidity of atmosphere: 20%<

Measurement Example 3

Raman spectrometry was performed on the specimen shown in FIG. 2, which is the same one as in Measurement Example 1, with the exciting ray directed to the central point (denoted by the arrow p) on one principal plane (orienting toward the incident light) of the oxide semiconductor electrode layer 33. In this way there was obtained the Raman spectrum (i) shown in FIG. 11. Incidentally, the Raman spectrometry was carried out under the following conditions.
Light source: DPSS
Wave length: 473 nm
Temperature of atmosphere: 25° C.
Humidity of atmosphere: 60%

Each of the Raman spectra indicated by "h" and "i" has the peak (indicated by the arrow c) attributable to the dye and the peak (indicated by the arrow d) attributable to the oxide semiconductor ($TiO_2$). The Raman spectrometry carried out in an atmosphere of high humidity (as in measurement example 3) gives the peak indicated by "i" (attributable to the oxide semiconductor electrode layer 33) which is low due to moisture existing in the atmosphere. This is not the case in measurement example 2 in which the Raman spectrometry carried out in a low-humidity atmosphere shows the high peak intensity attributable to the dye. This suggests that Raman spectrometry in a low-humidity atmosphere is desirable for reproducible determination of the dye adsorbed to the oxide semiconductor electrode layer 33.

Measurement Examples 4 and 5

These examples are intended to investigate how Raman spectrometry is affected by the exciting rays differing in wave length.

Measurement Example 4

Figure 12:
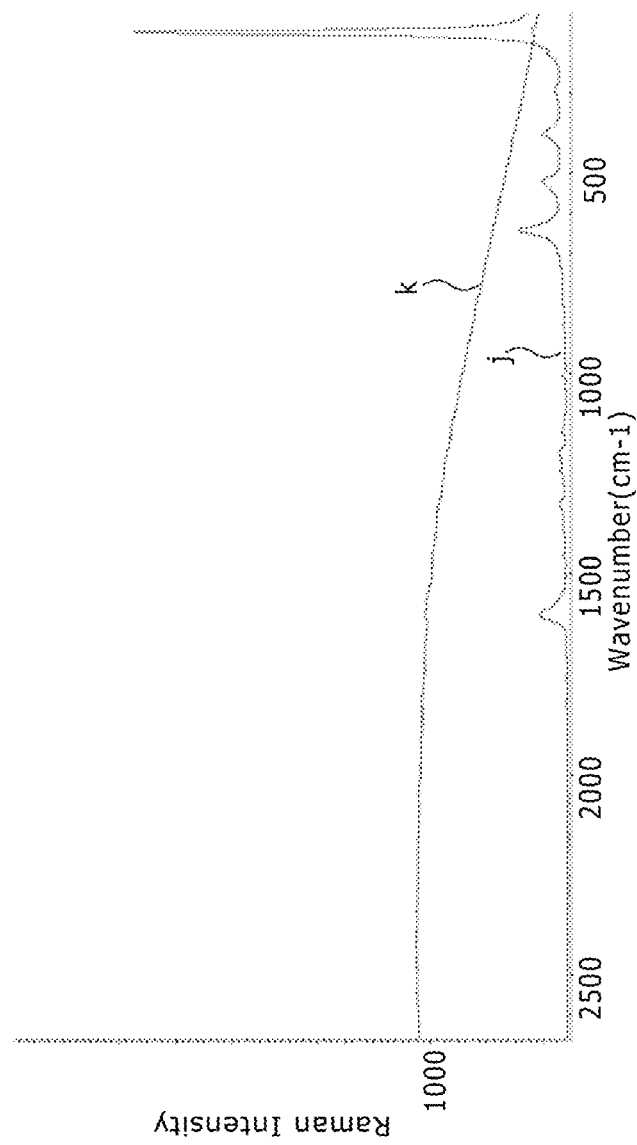
FIG. 12 is a diagram showing Raman spectra obtained under different conditions.

Raman spectrometry was performed on the specimen shown in FIG. 2, which is the same one as in Measurement Example 1, with the exciting ray directed to the central point (denoted by the arrow p) on one principal plane (orienting toward the incident light) of the oxide semiconductor electrode layer 33. In this way there was obtained the Raman spectrum (j) shown in FIG. 12. Incidentally, the Raman spectrometry was carried out under the following conditions.
Light source: YAG
Wave length: 1064 nm
Temperature of atmosphere: 20° C.
Humidity of atmosphere: 30%<

Measurement Example 5

Raman spectrometry was performed on the specimen shown in FIG. 2, which is the same one as in Measurement Example 1, with the exciting ray directed to the central point (denoted by the arrow p) on one principal plane (orienting toward the incident light) of the oxide semiconductor electrode layer 33. In this way there was obtained the Raman spectrum (k) shown in FIG. 12. Incidentally, the Raman spectrometry was carried out under the following conditions.
Light source: Ar
Wave length: 514 nm
Temperature of atmosphere: 20° C.
Humidity of atmosphere: 30%

The following is noted from the Raman spectra in Measurement Examples 4 and 5. The Raman spectrometry (for Measurement Example 5) that employs the exciting ray with a wave length of 514 nm in the visible region does not give any meaningful Raman spectrum on account of fluorescence emitted by the dye. This is not the case in Measurement Example 4 for which the Raman spectrometry employs the exciting ray with a wave length of 1064 nm in the infrared region. The resulting Raman spectrum is not affected by fluorescence. This suggests that the Raman spectrometry should employ the exciting ray with a wave length longer than 1000 nm in the infrared region. In this way it is possible to determine without influence of fluorescence the dye of various kinds adsorbed to the oxide semiconductor electrode layer 33.

Measurement Example 6

This example is intended to investigate how Raman spectrometry affects differently the parameter for dye adsorption quantity depending on the duration of dye adsorption. The specimens for measurement shown in FIG. 2 were prepared in the following way. First, the FTO base plate was coated with a paste of $TiO_2$, followed by baking in an electric furnace at 100 to 600° C. Thus there was obtained a porous sintered body of $TiO_2$. Then, it was immersed in a solution of ruthenium dye (Z907) dissolved in a mixture of tert-butanol and acetonitrile, so that the porous sintered body of $TiO_2$ was made to adsorb the sensitizing dye. The duration of adsorption was 30 minutes. In this way there was obtained the specimen for measurement as shown in FIG. 2.

Several specimens were prepared in the same way as above except that the duration of adsorption was changed to one, two, four, five, six, and seven hours.

Raman spectrometry was performed on the specimens, with the exciting ray directed to the central point (denoted by the arrow p in FIG. 2) and one point at the periphery on one principal plane (orienting toward the incident light) of the oxide semiconductor electrode layer 33. In this way there were obtained Raman spectra. The parameters for dye adsorption quantity were calculated. Incidentally, the Raman spectrometry was carried out under the following conditions.

Light source: DPSS
Wave length: 473 nm
Temperature of atmosphere: 20° C.
Humidity of atmosphere: 20%

Figure 13:
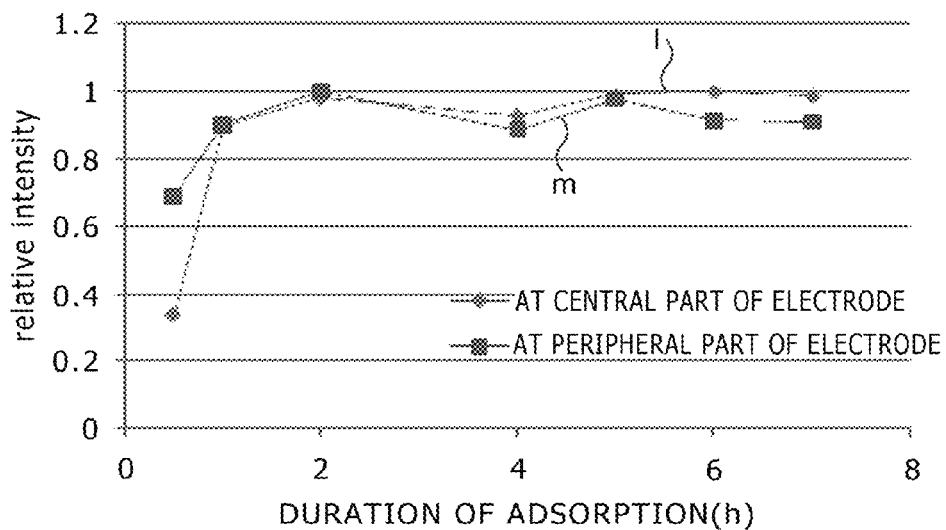
FIG. 13 is a graph in which the parameter for dye adsorption quantity is plotted against the duration of dye adsorption.

The thus obtained parameters for dye adsorption quantity were plotted against the duration of adsorption to give the graph shown in FIG. 13. The line denoted by "1" in FIG. 13 represents the graph of the parameters for dye adsorption quantity which were measured at the center of the oxide semiconductor electrode layer 33. Likewise, the line denoted by "m" in FIG. 13 represents the graph of the parameters for dye adsorption quantity which were measured at the periphery of the oxide semiconductor electrode layer 33. Comparison between the line 1 and the line m reveals that the parameters for dye adsorption quantity varies depending on the duration of adsorption. This suggests that the adsorption of dye proceeds differently at the center and periphery of one principal plane (orienting toward the incident light) of the oxide semiconductor electrode layer 33. The line 1 becomes flat after two hours of adsorption, and this flat region indicates that the amount of the adsorbed dye has reached saturation in the oxide semiconductor electrode layer 33.

Measurement Example 7

Acquisition of Parameters for Dye Adsorption Quantity at Several Measurement Points Several specimens were prepared which are identical with those in Measurement Example 1 except for conditions of dye adsorption. Each of these specimens was used as a constituent of the dye-sensitized solar cell. In addition, each of these specimen was examined for Raman spectrometry, with the exciting ray directed to several measurement points on one principal plane (orienting toward the incident light) of the oxide semiconductor electrode layer 33. From the resulting Raman spectra were calculated the parameters for dye adsorption quantity defined as (Peak intensity attributable to dye) divided by (Peak intensity attributable to oxide semiconductor).

The Raman spectrometry was carried out such that the exciting rays were directed to seven measurement points (s1 to s4, s6 to s8) and ten measurement points (t1 to t10) on one principal plane (orienting toward the incident light) of the oxide semiconductor electrode layer 33. From the resulting Raman spectra were calculated the parameters for dye adsorption quantity. From the thus obtained parameters were calculated their average, their standard deviation, and the coefficient of variation defined as [Standard deviation/Average value]×100%. Dye-sensitized solar cells, each provided with the specimen, were tested for the efficiency of power generation.

Figure 14:
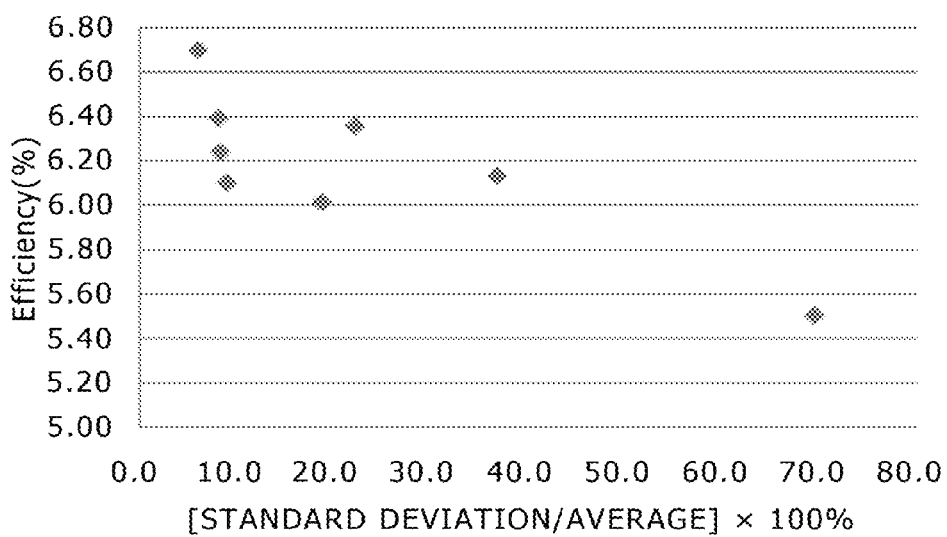
FIG. 14 is a graph in which the efficiency of power generation is plotted against the coefficient of variation of the parameters for dye absorption quantity.

The relation between the efficiency of power generation and the coefficient of variation ([Standard deviation/Average]×100%) is graphically shown in FIG. 14. It is noted from FIG. 14 that the efficiency of power generation increases according as the variation decreases.

Measurement Example 8

This example demonstrates the evaluation of the electrode by Raman mapping which was performed on the specimen (shown in FIG. 2) prepared in the following manner. First, an FTO base plate was coated with a paste of $TiO_2$, followed by baking in an electric furnace at 100 to 600° C. The FTO base plate having a sintered body of porous $TiO_2$ formed thereon was immersed in a solution of ruthenium dye (Z907) dissolved in a mixed solvent of tert-butanol and acetonitrile, so that the sintered body of porous $TiO_2$ adsorbed the dye. After dye adsorption for one hour or 1.5 hours, Raman mapping was performed on one principal plane (orienting toward the incident light) of the oxide semiconductor electrode layer 33.

Figures 15A, 15B:
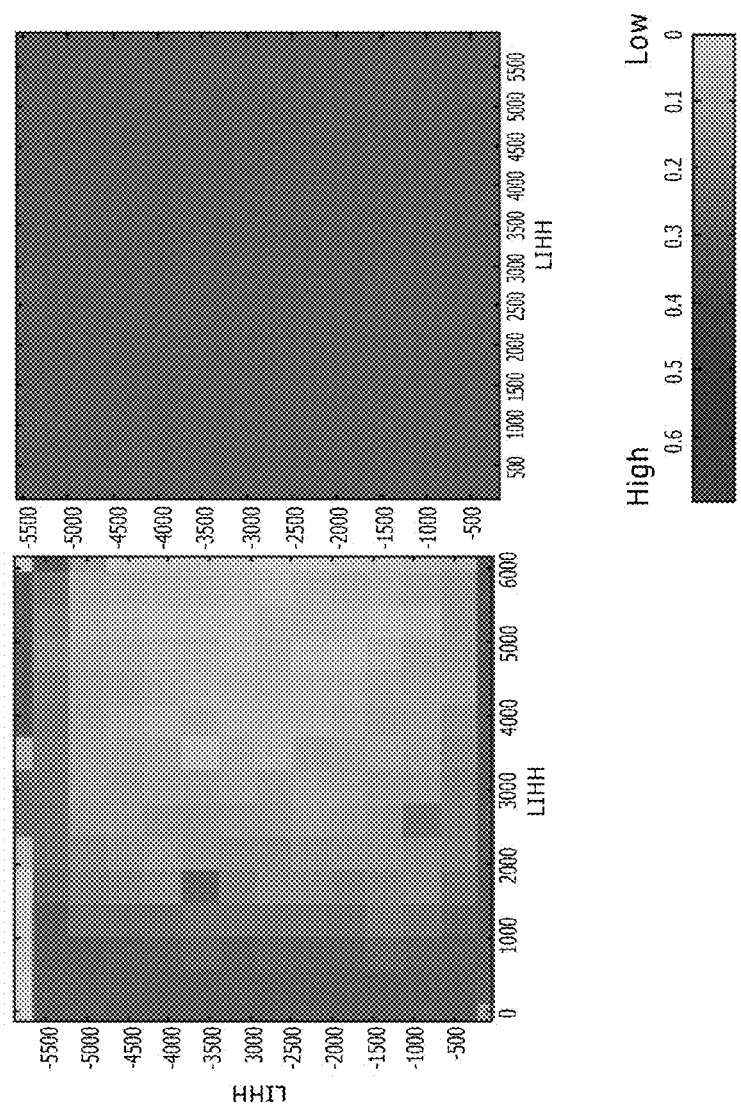
FIGS. 15A and 15B are images showing the distribution of the parameters for dye adsorption quantity, the image being a result of Raman mapping.

FIGS. 15A and 15B show the mapping data of the parameters for dye adsorption quantity. FIGS. 15A and 15B show the data obtained after adsorption for one hour and 1.5 hours, respectively. It is noted from these figures that the mapping data of the parameters for dye adsorption quantity on one principal plane (orienting toward the incident light) of the oxide semiconductor electrode layer 33 makes it possible to evaluate the amount and state of dye adsorption to the oxide semiconductor electrode layer 33. The mapping data shown in FIG. 15B suggests that the dye is uniformly adsorbed to the oxide semiconductor electrode layer 33.

8. Additional Embodiments

The present technology is not restricted to the foregoing embodiments but may be changed and modified variously within the scope thereof. The numerical values, structure, shape, materials, and process employed in the foregoing embodiments are mere examples, and they may be changed according to need. For example, the oxide semiconductor electrode may be modified such that the transparent conductive layer 13 on the base plate 12 is given a stripy pattern by etching and then coated with the oxide semiconductor electrode layer 33 which is also etched in a stripy pattern.

The present disclosure contains subject matter related to that disclosed in Japanese Priority Patent Application JP 2010-272496 filed in the Japan Patent Office on Dec. 7, 2010, the entire content of which is hereby incorporated by reference.

What is claimed is:

1. A method for evaluation of an oxide semiconductor electrode, said method comprising:
    performing Raman spectrometry on a porous oxide semiconductor layer having a dye adsorbed thereto, thereby acquiring a Raman spectrum having a peak attributable to the dye and a peak attributable to the oxide semiconductor;
    obtaining from the Raman spectrum a parameter for a dye adsorption quantity according to:

Parameter for dye adsorption quantity=(Peak intensity attributable to dye)/(Peak intensity attributable to oxide semiconductor); and estimating an amount of the dye adsorbed to the porous oxide semiconductor layer at least on a basis of the obtained parameter for dye adsorption quantity.

2. The method of claim 1, wherein said Raman spectrometry is performed with an exciting ray directed to a center of one principal plane of the oxide semiconductor layer, said principal plane orienting toward incident light.

3. The method of claim 2, wherein the amount of the dye adsorbed to the porous oxide semiconductor layer is regarded as having reached saturation in a case where the parameter for dye adsorption quantity exceeds a threshold value for saturation which represents a state in which the porous oxide semiconductor layer is saturated with the dye adsorbed thereto.

4. The method of claim 1, wherein the Raman spectrometry is performed in an atmosphere of low humidity.

5. The method of claim 1, wherein the Raman spectrometry employs an exciting ray with a wave length longer than 1000 nm in an infrared region.

6. A method for evaluation of an oxide semiconductor electrode, said method comprising:

performing Raman spectrometry with an exciting ray directed to several measurement points on one principal plane of a porous oxide semiconductor layer having a dye adsorbed thereto, said principal plane orienting toward incident light, thereby acquiring Raman spectra each having a peak attributable to the dye and a peak attributable to the oxide semiconductor;

obtaining from the Raman spectra parameters for dye adsorption quantity according to:

Parameter for dye adsorption quantity=(Peak intensity attributable to dye)/(Peak intensity attributable to oxide semiconductor); and estimating a state of the dye adsorbed to the porous oxide semiconductor layer at least on a basis of a variation of the obtained parameters for the dye adsorption quantity.

7. The method of claim 6, wherein measurement points include at least one point at a center of the principal plane and two points at intersections of one straight line passing through a central point and peripheral edges of the principal plane.

8. The method of claim 7, wherein the measurement points further include one or more points on said straight line on said principal plane in addition to one point at said center and two points at said peripheral edges.

9. The method of claim 8, wherein the measurement points further include two points at intersections of another straight line different from said straight line passing through the center on the principal plane and the peripheral edges of the principal plane and one or more points on said another straight line on said principal plane in addition to said one point at the center and said two points at the peripheral edges.

10. The method of claim 7, wherein the measurement points comprise at least ten measurement points.

11. The method of claim 6, which further comprises:
calculating a coefficient of variation according to (Standard deviation/Average)×100%, which denotes a variation of the parameters for dye adsorption quantity; and
evaluating the state of dye adsorption to the porous oxide semiconductor layer on the basis of the calculated coefficient of variation.

12. The method of claim 11, wherein the state of dye adsorption to the oxide semiconductor electrode is regarded as uniform in a case where the coefficient of variation is lower than a prescribed threshold value.

13. A method for evaluation of an oxide semiconductor electrode, said method comprising:

performing Raman mapping on one principal plane of a porous oxide semiconductor layer having a dye adsorbed thereto, said principal plane orienting toward incident light, thereby obtaining a distribution of parameters for dye adsorption quantity orienting toward the incident light according to:

Parameter for dye adsorption quantity=(Peak intensity attributable to dye)/(Peak intensity attributable to oxide semiconductor); and evaluating a state of dye adsorption to said porous oxide semiconductor layer at least on a basis of a distribution of said parameters for dye adsorption quantity.

14. An apparatus for evaluation of an oxide semiconductor electrode, said apparatus comprising:
a Raman spectrometer; and
an arithmetic processor,
said Raman spectrometer configured to perform Raman spectrometry on a central part of one principal plane of the oxide semiconductor electrode, said principal plane orienting toward incident light,
said arithmetic processor configured to calculate a parameter for a dye adsorption quantity from the Raman spectrum obtained by said Raman spectrometer according to:

Parameter for dye adsorption quantity=(Peak intensity attributable to dye)/(Peak intensity attributable to oxide semiconductor); and said arithmetic processor configured compare the calculated parameter for the dye adsorption quantity with a prescribed threshold value, and
said apparatus for evaluation regarding the oxide semiconductor electrode as having good characteristic properties in a case where the parameter for dye adsorption quantity exceeds the prescribed threshold value.

15. The apparatus of claim 14, further comprising:
a sample chamber configured to keep its atmosphere at low humidity.

16. An apparatus for production of an oxide semiconductor electrode, said apparatus comprising
a Raman spectrometer;
an arithmetic processor;
a controlling unit; and
a dye solution feeder, wherein
said Raman spectrometer is configured to perform Raman spectrometry on several measurement points on one principal plane of the oxide semiconductor electrode, said principal plane orienting toward incident light,
said arithmetic processor configured to calculate a parameter for a dye adsorption quantity from each Raman spectrum obtained by said Raman spectrometer according to:

Parameter for dye adsorption quantity=(Peak intensity attributable to dye)/(Peak intensity attributable to oxide semiconductor); and said arithmetic processor configured to calculate a coefficient of variation of the parameter for dye adsorption quantity according to (Standard deviation/Average)× 100%,
said controlling unit configured to compare the coefficient of variation with a prescribed threshold value, and to give feedback control to the dye solution feeder to control its feeding action.

17. The apparatus of claim 16, wherein measurement points include at least one point at a center of the principal plane and two points at intersections of one straight line passing through a central point and peripheral edges of the principal plane.

* * * * *